US006797755B1

(12) United States Patent
Meier et al.

(10) Patent No.: US 6,797,755 B1
(45) Date of Patent: Sep. 28, 2004

(54) STABILIZERS AND ANTIOZONANTS FOR ELASTOMERS

(75) Inventors: Hans-Rudolf Meier, Basel (CH); Gerrit Knobloch, Magden (CH); Samuel Evans, Marly (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 83 days.

(21) Appl. No.: 10/110,620

(22) PCT Filed: Oct. 10, 2000

(86) PCT No.: PCT/EP00/09928

§ 371 (c)(1),
(2), (4) Date: Apr. 15, 2002

(87) PCT Pub. No.: WO01/29126

PCT Pub. Date: Apr. 26, 2001

(30) Foreign Application Priority Data

Oct. 18, 1999 (CH) ................................. 190199

(51) Int. Cl.⁷ ................................. C08L 5/41
(52) U.S. Cl. ................. 524/155; 524/236; 524/240; 524/247; 524/249; 524/251; 524/252; 524/392; 524/571; 524/575.5
(58) Field of Search ............... 524/295, 392, 524/236, 240, 571, 575.5, 247, 249, 251, 252

(56) References Cited

U.S. PATENT DOCUMENTS

| 4,072,654 | A | * | 2/1978 | Kline .......................... 524/244 |
| 5,002,698 | A | * | 3/1991 | Wirth et al. ................. 252/475 |
| 6,365,653 | B1 | * | 4/2002 | Meier et al. ................. 524/155 |

FOREIGN PATENT DOCUMENTS

| EP | 0233140 | 8/1987 | |
| EP | 0331608 | 9/1989 | |
| EP | 0 916 695 A1 | * 5/1998 | ........... C08K/5/372 |
| EP | 0916695 | 5/1999 | |

OTHER PUBLICATIONS

Derwent Abstr. 1975–08225W for JP 49066731 (1974).
English Abstract for EP 0916695 (1999).
R. A Mazzeo et al., "Tire Technology International", 1994, pp. 36–46.

D. Miller et al., Rubber World, vol. 200 (5), pp. 13–23, (1989).

* cited by examiner

Primary Examiner—David W. Wu
Assistant Examiner—Rip A Lee
(74) Attorney, Agent, or Firm—Tyler A. Stevenson

(57) ABSTRACT

Elastomers which have excellent stability to prevent oxidative, thermal, dynamic, light-induced and/or ozone-induced degradation comprise, as stabilizers, at least one compound of the formula (I): $[R-S(=O)_m-CH_2-CH(OH)-CH_2]_n-N(R^1)_{2-n}-R^2$, in which R is $C_4-C_{20}$alkyl, hydroxyl-substituted $C_4-C_{20}$alkyl; phenyl, benzyl, α-methylbenzyl, α,α-dimethylbenzyl, cyclohexyl or $-(CH_2)_qCOOR^3$, and, if m is 0, R may additionally be (a); and, if n is 1 and $R^4$ is hydrogen, R may additionally be $R^2-R^1N-CH_2-CH(OH)-CH_2-S(=O)_m-(CH_2)_x-$ or $R^2-R^1N-CH_2-CH(OH)-CH_2-S(=O)_m-CH_2-CH_2-(OCH_2-CH_2)_y-$, $R^1$ is hydrogen, cyclohexyl or $C_3-C_{12}$alkyl, $R^2$ is (b), $R^3$ is $C_1-C_{18}$alkyl, $R^4$ is hydrogen or $-CH_2-CH(OH)-CH_2-S(=O)_m-R$, X is $C_1-C_8$alkyl, Y is $C_1-C_8$alkyl, m is 0 or 1, n is 1 or 2, q is 1 or 2, x is from 2 to 6, and y is 1 or 2. The compounds of the formula (I) are also suitable as stabilizes for elastomers to prevent contact discoloration of substrates coming into contact with elastomers.

(a)

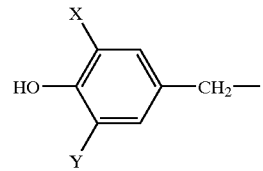

(b)

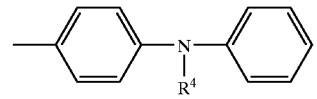

13 Claims, No Drawings

STABILIZERS AND ANTIOZONANTS FOR ELASTOMERS

The present invention relates to compositions comprising an elastomer susceptible to oxidative, thermal, dynamic, or light- and/or ozone-induced degradation and, as stabilizer, at least one compound of the S-substituted 4-(3-mercapto/sulfinyl-2-hydroxypropylamino)diphenylamine type, and also to the use of the stabilizers to prevent contact discoloration of substrates coming into contact with elastomers, and as antiozonants for elastomers to prevent oxidative, thermal, dynamic, or light- and/or ozone-induced degradation, and also to a process for preventing contact discoloration of substrates coming into contact with elastomers, and to a process for stabilizing elastomers, which comprises incorporating into these, or applying to these, at least one compound of the S-substituted 4-(3-mercapto/sulfinyl-2-hydroxypropylamino)diphenylamine type.

Rubber products (vulcanizates), like all polymers, are susceptible to oxidative, thermal, dynamic or light-induced degradation. A particular factor causing damage to diene rubber vulcanizates is ozone. Ozone attacks the carbon-carbon double bonds, of which many remain in the rubber (vulcanizate), and, via the mechanism known as ozonolysis, causes damage which is apparent as typical surface cracking, and failure of the rubber product. The damage is particularly serious when the rubber product is under dynamic stress.

To prevent ozone damage, antioxidants selected from the class consisting of para-phenylenediamines [see Russel A. Mazzeo et al., "Tire Technology International" 1994, pp. 36–46; or Donald E. Miller et al., Rubber World, 200 (5), 13–23 (1989)] are generally added to vulcanizates. These compounds have very good protective action, especially under dynamic conditions, but develop a strong intrinsic colour (discolouring) and, as a result of high migration rate, these compounds give severe contact discoloration (staining), i.e. the dye transfers to other substrates/products on direct contact. This means that the stabilizers employed in the prior art cannot be used as stabilizers for rubber products which are free from carbon black or are "non-black", and they are also unsuitable for (black) rubber products which comprise carbon black and are intended for use in direct contact with pale-coloured products.

There continues, therefore, to be a need for colour-stable stabilizers which prevent ozone damage to rubber products, in particular to pale-coloured rubber products. There also continues to be a need for stabilizers which, although they may have an intrinsic colour, are unable, for example as a result of chemical bonding to the rubber chains, to transfer the colour to other products.

The use of compounds of the 1-alkylthio-2-hydroxy-3-aminopropane type as stabilizers for lubricants, hydraulic fluids or metalworking fluids is known from U.S. Pat. No. 4,863,621, for example.

It has now been found that compounds of the S-alkylated 4-(3-mercapto/sulfinyl-2-hydroxypropylamino) diphenylamine type are particularly suitable as stabilizers for elastomers susceptible to oxidative, thermal, dynamic, or light- and/or ozone-induced degradation.

The present invention therefore provides compositions comprising a) a naturally occurring or synthetic elastomer susceptble to oxidative, thermal, dynamic, light-induced and/or ozone-induced degradation, and b) as stabilizer, at least one compound of the formula I

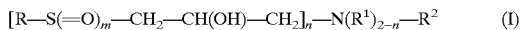

in which

R is $C_4$–$C_{20}$alkyl, hydroxyl-substituted $C_4$–$C_{20}$alkyl; phenyl, benzyl, α-methylbenzyl, α,α-dimethylbenzyl, cyclohexyl or —$(CH_2)_q COOR^3$, and, if m is 0, R may additionally be

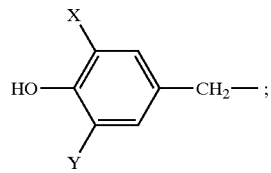

and, it n is 1 and $R^4$ is hydrogen, R may additionally be $R^2$—$R^1$N—$CH_2$—$CH(OH)$—$CH_2$—$S(=O)_m$—$(CH_2)_x$— or $R^2$—$R^1$N—$CH_2$—$CH(OH)$—$CH_2$—$S(=O)_m$—$CH_2$—$CH_2$—$(O$—$CH_2$—$CH_2)_y$—, $R^1$ is hydrogen, cyclohexyl or $C_3$–$C_{12}$alkyl, $R^2$ is

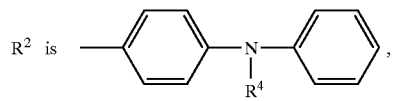

$R^3$ is $C_1$–$C_{18}$alkyl, $R^4$ is hydrogen or —$CH_2$—$CH(OH)$—$CH_2$—$S(=O)_m$—R, X is $C_1$–$C_8$alkyl, Y is $C_1$–$C_8$alkyl, m is 0 or 1, n is 1 or 2, q is 1 or 2, x is from 2 to 6, and y is 1 or 2.

Alkyl having up to 20 carbon atoms is a branched or unbranched radical, such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl or eicosyl. One of the preferred meanings of R is $C_4$–$C_{20}$alkyl, in particular $C_6$–$C_{12}$alkyl, e.g. $C_8$–$C_{12}$alkyl. A particularly preferred meaning of R is tert-nonyl. One of the preferred meanings of $R^1$ is $C_3$–$C_{12}$alkyl, in particular $C_3$–$C_8$alkyl, e.g. $C_3$–$C_6$alkyl. A particularly preferred meaning of $R^1$ is isopropyl or 1,3-dimethylbutyl. A particularly preferred meaning of $R^3$ is $C_1$–$C_{18}$alkyl, in particular $C_4$–$C_{12}$alkyl, e.g. $C_6$–$C_8$alkyl. A preferred meaning of X and Y is $C_1$–$C_8$alkyl, in particular $C_1$–$C_4$alkyl, e.g. methyl or tert-butyl.

Hydroxyl-substituted $C_4$–$C_{20}$alkyl is a branched or unbranched radical preferably having from 1 to 3, in particular 1 or 2, hydroxyl groups, for example hydroxyethyl, 3-hydroxypropyl, 2-hydroxypropyl, 4-hydroxybutyl, 3-hydroxybutyl, 2-hydroxybutyl, 5-hydroxypentyl, 4-hydroxypentyl, 3-hydroxypentyl, 2-hydroxypentyl, 6-hydroxyhexyl, 5-hydroxyhexyl, 4-hydroxyhexyl, 3-hydroxyhexyl, 2-hydroxyhexyl, 7-hydroxyheptyl, 6-hydroxyheptyl, 5-hydroxyheptyl, 4-hydroxyheptyl, 3-hydroxyheptyl, 2-hydroxyheptyl, 8-hydroxyoctyl, 7-hydroxyoctyl, 6-hydroxyoctyl, 5-hydroxyoctyl, 4-hydroxyoctyl, 3-hydroxyoctyl, 2-hydroxyoctyl, 9-hydroxynonyl, 10-hydroxydecyl, 11-hydroxyundecyl, 12-hydroxydodecyl, 13-hydroxytridecyl, 14-hydroxytetradecyl, 15-hydroxypentadecyl, 16-hydroxyhexadecyl, 17-hydroxyheptadecyl, 18-hydroxyoctadecyl or 20-hydroxyeicosyl. A preferred meaning of R is hydroxyl-substituted $C_4$–$C_{12}$alkyl, in particular hydroxyl-substituted $C_5$–$C_{12}$alkyl, e.g. hydroxyl-substituted $C_5$–$C_{11}$alkyl.

Interesting compositions comprise, as component b), at least one compound of the formula I in which, if n is 2, R and $R^3$ have the same meanings.

Preferred compositions comprise, as component b), at least one compound of the formula I in which R is $C_4$–$C_{12}$alkyl, hydroxyl-substituted $C_4$–$C_{12}$alkyl; benzyl, α-methylbenzyl, cyclohexyl or —$(CH_2)_q COOR^3$, and, if n is 1, R may additionally be

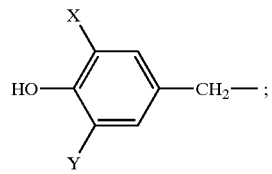

and, if n is 1 and $R^4$ is hydrogen, R may additionally be $R^2$—$R^1N$—$CH_2$—$CH(OH)$—$CH_2$—$S(=O)_m$—$(CH_2)_x$— or $R^2$—$R^1N$—$CH_2$—$CH(OH)$—$CH_2$—$S(=O)_m$—$CH_2$—$CH_2$—$(O$—$CH_2$—$CH_2)_y$—, $R^1$ is hydrogen, cyclohexyl or $C_3$–$C_8$alkyl, $R^3$ is $C_4$–$C_{12}$alkyl, X is $C_1$–$C_4$alkyl, Y is $C_1$–$C_4$alkyl, m is 0 or 1, q is 1 or 2, x is from 2 to 4, and y is 1 or 2.

Preference is also given to compositions comprising, as component b), at least one compound of the formula I in which R is $C_6$–$C_{12}$alkyl, hydroxyl-substituted $C_6$–$C_{12}$alkyl; benzyl or —$(CH_2)_q COOR^3_1$, and, if n is 1 and $R^4$ is hydrogen, R may additionally be $R^2$—$R^1N$—$CH_2$—$CH(OH)$—$CH_2$—$S(=O)_m$—$(CH_2)_x$— or $R^2$—$R^1N$—$CH_2$—$CH(OH)$—$CH_2$—$S(=O)_m$—$CH_2$—$CH_2(OCH_2$—$CH_2)_y$—, $R^1$ is cyclohexyl or $C_3$–$C_8$alkyl, $R^3$ is $C_6$–$C_{10}$alkyl, m is 0 or 1, q is 1 or 2, x is 2, and y is 1 or 2.

Particular preference is given to compositions comprising, as component b), at least one compound of the formula I in which R is $C_8$–$C_{12}$alkyl or —$(CH_2)_q COOR^3$, and, if n is 1 and $R^4$ is hydrogen, R may additionally be $R^2$—$R^1N$—$CH_2$—$CH(OH)$—$CH_2$—$S(=O)_m$—$CH_2$—$CH_2$—$(O$—$CH_2$—$CH_2)_y$—, $R^1$ is isopropyl or 1,3-dimethylbutyl, $R^2$ is 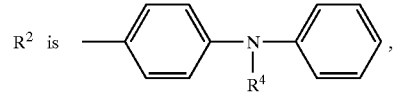

$R^3$ is $C_6$–$C_8$alkyl, $R^4$ is hydrogen or —$CH_2$—$CH(OH)$—$CH_2$—$S(=O)_m$—R, m is 0 or 1, n is 1 or 2, q is 1, and y is 1 or 2.

Compounds of the formula I may, for example, be prepared in a manner similar to that of Example 1 disclosed in U.S. Pat. No. 4,863,621, by reacting the epoxides of the formula II with the amines of the formula III

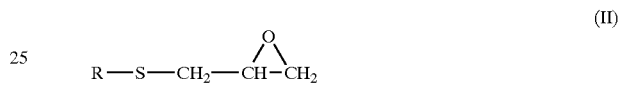

The reaction takes place in the melt or in the presence of a suitable protic or aprotic solvent, such as xylene, ethanol or 2-propanol. The reaction preferably takes place in the presence of a suitable catalyst, e.g. salicylic acid or Fulcat 22B, in amounts of from 0.05 to 10%, in particular 0.5 to 5%, based on the total weight of the compounds of the formulae II and III.

The reaction is carried out at temperatures of from 100 to 220° C., for example, in particular at from 110 to 170° C., e.g. at from 120 to 150° C. During the reaction it is preferable for the compound of the formula II to be used in a molar excess over the compound of the formula III. A specifically preferred molar ratio of the compound of the formula II to the compound of the formula III is from 1.05:1 to 1.5:1.

The compounds of the formula I in which m is 1 (sulfoxides) may be obtained by known methods, for example, from the compounds of the formula I in which m is 0 (thioethers), by oxidation. An example of a suitable and specifically preferred oxidant is hydrogen peroxide.

Oxidation of the thioethers with an oxidant, such as hydrogen peroxide, can also give sulfinyl compounds which, in the case where n=2, have been oxidized at only one sulfur. If the radical $R^4$ contains sulfur, oxidation of this sulfur is also possible, and mixtures of compounds can therefore be produced which have each been oxidized or not at the appropriate sulfur. All conceivable permutations are possible. These mixtures are likewise suitable as good stabilizers for elastomers, to prevent their oxidative, thermal, dynamic, or light- and/or ozone-induced degradation, and/or as stabilizers to prevent contact discoloration of substrates coming into contact with elastomers.

The compounds of the formulae II and III are known from the literature and are in some cases commercially available.

Component b) is suitable for stabilizing elastomers, in particular pale-coloured elastomers, to prevent oxidative, thermal, dynamic, or light- and/or ozone-induced degradation.

Elastomers are to be understood as meaning macromolecular materials which after considerable deformation under a small load at room temperature rapidly regain approximately their original shape. See also Hans-Georg Elias, "An Introduction to Polymer Science", Section 12. "Elastomers", pp. 388–393, 1997, VCH Verlagsgesellschaft mbH, Weinheim, Germany or "Ullmann's Encyclopedia of Industrial Chemistry, fifth, completely revised edition, Volume A 23", pp. 221–440 (1993).

Examples of elastomers which may be present in the compositions of the invention are the following materials:
1. Polymers of diolefins, for example polybutadiene or polyisoprene.
2. Copolymers of mono- and diolefins with one another or with other vinyl monomers, e.g. propylene-isobutylene copolymers, propylene-butadiene copolymers, isobutylene-isoprene copolymers, ethylene-alkyl acrylate copolymers, ethylene-alkyl methacrylate copolymers, ethylene-vinyl acetate copolymers, acrylonitrile-butadiene copolymers, and also terpolymers of ethylene with propylene and with a diene, such as hexadiene, dicyclopentadiene or ethylidenenorbornene.
3. Copolymers of styrene or α-methylstyrene with dienes or with acrylic derivatives, e.g. styrene-butadiene, styrene-butadiene-alkyl acrylate and styrene-butadiene-alkyl methacrylate; block copolymers of styrene, e.g. styrene-butadiene-styrene, styrene-isoprene-styrene and styrene-ethylenebutylene-styrene, and also adhesives prepared from the latter three.
4. Halogen-containing polymers, e.g. polychloroprene, chlorinated rubber, chlorinated or brominated copolymer of isobutylene-isoprene (halobutyl rubber).
5. Natural rubber.
6. Aqueous emulsions of natural or synthetic rubbers, e.g. natural rubber latex or latices of carboxylated styrene-butadiene copolymers.

The elastomers to be protected are preferably vulcanized elastomers. Of particular interest are natural rubber and synthetic rubber, and vulcanizates prepared therefrom. Particular preference is given to polydiene vulcanizates, halogen-containing polydiene vulcanizates, polydiene copolymer vulcanizates, in particular styrene-butadiene copolymer vulcanizates, and ethylene-propylene terpolymer vulcanizates.

Component b) is usefully added to the elastomer to be stabilized in amounts of from 0.05 to 10%, for example from 0.1 to 5%, preferably from 0.5 to 3.0%, based on the weight of the elastomer to be stabilized.

In addition to components a) and b), the compositions of the invention may comprise other additives, such as the following:
1. Antioxidants
    1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
    1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
    1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octade-cyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.
    1.4. Tocopherols, for example α-tocopherol, β-tocopherol, γ-tocopherol, δ-tocopherol and mixtures thereof (vitamin E).
    1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methytphenol), 4,4'-thiobis(3,6-di-sec-amylphenol), 4,4'-bis(2,6-dimethyl-4-hydroxyphenyl)disulfide.
    1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenylterephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.
    1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.
    1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.
    1.9. Aromatic hydroxybenzyl compounds, for example 1,3,5-tris(3,5-di-tert-butyl-4-hydroxybenzyl)-2,4,6- trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyamino)-1,3,5-triazine, 2-octylmercapto-4,6-bis(3,5-di-tert-butyl-4-hydroxyamino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3butyl-4-hydroxy-5-methylphenyl)propionyloxy}-1,1-dimethylethyl]-2,4,8,10-tetraoxaspiro[5,5]undecane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyhenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamine, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard® XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetra-methyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene.

2. UV absorbers and Light Stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)

benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$—CH$_2$—COO—CH$_2$CH$_2$—]$_2$, where R=3'-tert-butyl-4'-hydroxy-5'-2H-benzotazol-2-ylphenyl, 2-[2'-hydroxy-3'-(α,α-dimethylbenzyl)-5'-(1,1,3,3-tetramethylbutyl)phenyl]-benzotriazole; 2-[2'-hydroxy-3'-(1,1,3,3-tetramethylbutyl)-5'-(α,α-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-α-methyl-p-methoxycinnamate, methyl (α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl)n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-di-chloro-1,3,5-triazine, tris(2,2,6,6-tetramethyl-4-piperidyl) nitrilotriacetate, tetrakis(2,2,6,6-tetra-methyl-4-piperidyl)-1, 2,3,4-butanetetracarboxylate, 1,1'-(1,2-ethanediyl)-bis(3,3, 5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4,5]decane-2,4-dione, bis(1-octyl-oxy-2,2,6,6-tetramethylpiperidyl) sebacate, bis(i-octyloxy-2,2,6,6-tetramethylpiperidyl) succinate, linear or cyclic condensates of N,N'-bis(2,2,6,6-tetramethyl-4-piperidyl)hexamethylene-diamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4,5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-tri-chloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2, 6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-di-aza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6, 6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly(methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyl-oxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy) phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethyl-phenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl)phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,4-di-cumylphenyl) pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosyneraistic compounds, for example thiodipropionic acid dilauryl ester or thiodipropionic acid distearyl ester or compounds of formula IV

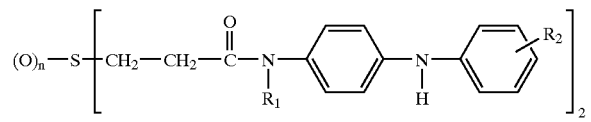
(IV)

wherein
$R_1$ is hydrogen,
$C_1$–$C_{12}$alkyl, cyclohexyl, phenyl or benzyl,
$R_2$ is hydrogen or $C_1$–$C_4$alkyl, and
n is the number 0, 1 or 2.

8. Peroxide scavengers, for example esters of 0-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

10. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene) sorbitol, 1,3:2,4-di(paramethyldibenzylidene)sorbitol, and 1,3:2,4-di(benzylidene)sorbitol.

11. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

12. Other additives, for example plasticisers, lubricants, emulsifiers, pigments, rheology additives, catalysts, flow-control agents, optical brighteners, flameproofing agents, antistatic agents and blowing agents.

13. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butylbenzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

Preferred compositions of the invention comprise, as other additives, one or more components selected from the group consisting of pigments, dyes, fillers, levelling assistants, dispersants, plasticizers, vulcanization activators, vulcanization accelerators, vulcanizers, charge control agents, adhesion promoters, light stabilizers or antioxidants, such as phenolic antioxidants (items 1.1 to 1.18 in the list) or aminic antioxidants (item 1.19 in the list), organic phosphites or phosphonites (item 4 in the list) and/or thiosynergists (item 7 in the list).

An example of the concentrations at which these other additives are added is from 0.01 to 10%, based on the total weight of the elastomer to be stabilized.

Component b), and also, if desired, other additives are incorporated into the elastomer by known methods, for example during mixing in internal mixers with rams (Banbury), on mixing rolls or in mixing extruders, prior to or during shaping or vulcanization, or else by applying dissolved or dispersed component b) to the elastomer, if desired with subsequent removal of the solvent by evaporation. When added to the elastomer to be stabilized, component b) and, if desired, other additives may also be in the form of a masterbatch comprising these, for example at a concentration of from 2.5 to 25% by weight.

Component b) and, if desired, other additives may also be added prior to or during the polymerization of synthetic elastomers or prior to crosslinking, i.e. advantageously, if desired, as a first-level stabilizer in the crude rubber, which may also comprise other components, such as carbon black as filler and/or extender oils.

The compounds of the formula I are bonded chemically to polymer chains under processing conditions (mixing, vulcanization, etc.). The compounds of the formula I are resistant to extraction, i.e. they continue to offer good protection after the substrate is subjected to intensive extraction. The loss of compounds of the formula I from the elastomer via migration or extraction is extremely slight.

The elastomers stabilized with the compounds of the formula I also show markedly improved and desirable gloss. This means that the surface gloss of the elastomer stabilized according to the invention, after exposure to ozone, is significantly higher than that of an unstabilized elastomer or of an elastomer stabilized in accordance with the prior art.

Component b) and, if desired, other additives may be in pure form or encapsulated in waxes, in oils or in polymers when they are incorporated into the elastomer to be stabilized.

Component b) and, if desired, other additives may also be sprayed onto the elastomer to be stabilized. They are capable of diluting other additives (e.g. the conventional additives given above) or melts of these, and they may therefore also be sprayed together with these additives onto the elastomer to be stabilized.

The resultant stabilized elastomers may be used in a wide variety of forms, e.g. ribbons, moulding compositions, profiles, conveyor belts or tyres (pneumatic).

The present invention further provides a process for stabilizing elastomers to prevent oxidative, thermal, dynamic, light-induced and/or ozone-induced degradation, which comprises incorporating into these or applying to these at least one component b).

The present invention further provides a process for preventing contact discoloration of substrates coming into contact with elastomers, which comprises incorporating into the elastomers, or applying to these, at least one component b).

A further embodiment of the present invention is the use of component b) as stabilizers for elastomers to prevent oxidative, thermal, dynamic, light-induced and/or ozone-induced degradation.

A further embodiment of the present invention is the use of component b) as stabilizers for elastomers to prevent contact discoloration of substrates coming into contact with elastomers.

The preferred compounds of the formula I [component b)] for the processes and uses listed above are the same as those for the compositions of the invention.

The present invention further provides novel compounds of the formula I

[R—S(=O)$_m$—CH$_2$—CH(OH)—CH$_2$]$_n$—N(R$^1$)$_{2-n}$—R$^2$    (I), in which

R is C$_4$–C$_{20}$alkyl, hydroxyl-substituted C$_4$–C$_{20}$alkyl; phenyl, benzyl, α-methylbenzyl, α,α-dimethylbenzyl, cyclohexyl or —(CH$_2$)$_q$COOR$^3$, and, if m is 0, R may additionally be

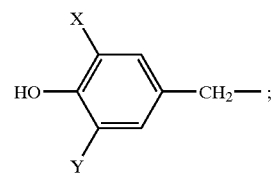

and, if n is 1 and R$^4$ is hydrogen, R may additionally be

R$^2$—R$^1$N—CH$_2$—CH(OH)—CH$_2$—S(=O)$_m$—(CH$_2$)$_x$— or

R$^2$—R$^1$N—CH$_2$—CH(OH)—CH$_2$—S(=O)$_m$—CH$_2$—CH$_2$(OCH$_2$—CH$_2$)$_y$—,

R$^1$ is hydrogen, cyclohexyl or C$_3$–C$_{12}$alkyl,

R$^2$ is 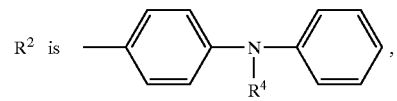,

R$^3$ is C$_1$–C$_{18}$alkyl,

R$^4$ is hydrogen or —CH$_2$—CH(OH)—CH$_2$—S(=O)$_m$—R,

X is C$_1$–C$_8$alkyl,

Y is C$_1$–C$_8$alkyl, m is 0 or 1, n is 1 or 2, q is 1 or 2, x is from 2 to 6, and y is 1 or 2; with the proviso that the compound of the formula Ia

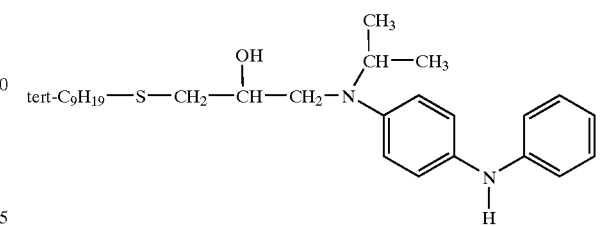

is excluded.

The preferred meanings of the general symbols in the novel compounds of the formula I are the same as the preferred meanings of the general symbols set out in relation to the compositions of the invention.

Interesting novel compounds of the formula I are those in which

R is C$_4$–C$_{20}$akyl, hydroxyl-substituted C$_4$–C$_{20}$alkyl; phenyl, benzyl, α-methylbenzyl, α,α-dimethylbenzyl, cyclohexyl or —(CH$_2$)$_q$COOR$^3$, R$^1$ is hydrogen, cyclohexyl or C$_3$–C$_{12}$alkyl, R$^2$ is 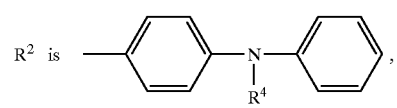, R$^3$ is C$_1$–C$_{18}$alkyl, R$^4$ is hydrogen or —CH$_2$—CH(OH)—CH$_2$—S(=O)$_m$—R, m is 0 or 1, n is 1 or 2, and q is 1 or 2, with the proviso that the compound of the formula Ia is excluded.

Preferred novel compounds of the formula I are those in which

R is $C_8$–$C_{12}$alkyl or —$(CH_2)_q$COOR$^3$, and, if n is 1 and R$^4$ is hydrogen, R may additionally be R$^2$—R$^1$N—CH$_2$—CH(OH)—CH$_2$—S(=O)$_m$—CH$_2$—CH$_2$—(O—CH$_2$—CH$_2$)$_y$—, R$^1$ is isopropyl or 1,3-dimethylbutyl,

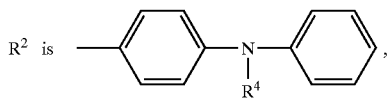

R$^3$ is $C_6$–$C_8$alkyl,

R$^4$ is hydrogen or —CH$_2$—CH(OH)—CH$_2$—S(=O)$_m$—R, m is 0 or 1, n is 1 or 2, q is 1, and y is 1 or 2, with the proviso that the compound of the formula Ia is excluded.

The examples below further illustrate the invention. Data in parts or percentages are based on weight.

EXAMPLE 1

Preparation of 4-{N-isopropyl-N-[3-(n-octylthio)-2-hydroxypropyl]amino}diphenylamine (Compound 101, Table 1)

A mixture of glycidyl n-octyl thioether (31.6 g) and 4-isopropylaminodiphenylamine [27.2 g, Vulkanox 4010 (RTM), Bayer] and salicylic acid (0.8 g) is stirred for 8 hours at 150° C. The reaction mixture is diluted with hexane and washed with saturated sodium carbonate solution and water. Concentration of the organic phase by evaporation followed by drying at 220° C./0.02 mbar gives 51.2 g (99.5%) of 4-{N-isopropyl-N-[3-(n-octylthio)-2-hydroxypropyl]amino}diphenylamine (compound 101, Table 1) as a viscous oil. Empirical formula $C_{26}H_{40}N_2OS$ (428.68). Analysis calculated: C, 72.85; H, 9.41; N, 6.53; S, 7.48%. Analysis found: C, 71.94; H, 9.63; N, 5.87; S, 7.86%. EI-MS: 428 (M$^+$), 239 (M minus the radical octyl-SCH$_2$CH(OH), base peak).

In a manner similar to that of Example 1 and using glycidyl tert-nonyl thioether instead of glycidyl n-octyl thioether, 98% of 4-{N-isopropyl-N-[3-(tert-nonylthio)-2-hydroxypropyl]-amino}diphenylamine (compound 102, Table 1) is obtained as a viscous oil. Molecular weight $C_{27}H_{42}N_2OS$ (M 442.71). Analysis calculated: C, 73.25; H, 9.56; N, 6.33; S, 7.24%. Analysis found: C, 73.21; H, 9.70; N, 6.26; S, 7.33%. EI-MS: 442 (M$^+$), 239 (M minus tert-nonyl-SCH$_2$CH(OH), base peak).

Again, in a manner similar to that of Example 1 and using glycidyl n-dodecyl thioether, glycidyl tert-dodecyl thioether or glycidyl isooctyloxycarbonylmethyl thioether instead of glycidyl n-octyl thioether, compounds 103, 104 and 111 (Table 1) are prepared.

In a manner similar to that of Example 1 and using 4-(1,3-dimethylbutylamino)diphenylamine instead of 4-isopropylaminodiphenylamine, compound 107 (Table 1) is obtained. Additionally replacing glycidyl n-octyl thioether with glycidyl n-dodecyl thioether, glycidyl tert-dodecyl thioether or glycidyl tert-nonyl thioether gives compounds 105, 106 and 108 (Table 1).

In a manner similar to that of Example 1, the reaction of glycidyl n-dodecyl thioether with 4-(2-octylamino) diphenylamine gives compound 109 (Table 1). Again in a manner similar to that of Example 1, the reaction of glycidyl n-dodecyl thioether with 4-cyclohexylaminodiphenylamine gives compound 110 (Table 1).

TABLE 1

R—S—CH$_2$—CH(OH)—CH$_2$—N(R$^1$)—C$_6$H$_4$—NH—C$_6$H$_5$  (101) to (111)

| Compound | R | R$^1$ | Constitution | M$^+$ |
|---|---|---|---|---|
| 101 | n-octyl | isopropyl | viscous oil | 428 |
| 102 | tert-nonyl | isopropyl | viscous oil | 442 |
| 103 | n-dodecyl | isopropyl | brown mass | 484 |
| 104 | tert-dodecyl | isopropyl | viscous oil | 484 |
| 105 | n-dodecyl | 1,3-dimethylbutyl | dark brown oil | 526 |
| 106 | tert-dodecyl | 1,3-dimethylbutyl | dark brown oil | 526 |
| 107 | n-octyl | 1,3-dimethylbutyl | dark brown oil | 470 |
| 108 | tert-nonyl | 1,3-dimethylbutyl | dark brown resin | 484 |
| 109 | n-dodecyl | 2-octyl | dark brown resin | 554 |
| 110 | n-dodecyl | cyclohexyl | dark brown resin | 524 |
| 111 | iso-$C_8H_{17}$OOCCH$_2$— | isopropyl | dark brown oil | 486 |

EXAMPLE 2

Preparation of 4-{N-isopropyl-N-[3-(n-octylsulfinyl)-2-hydroxypropyl]amino} diphenylamine (Compound 201, Table 2)

4.53 g of 30% strength aqueous hydrogen peroxide solution (H$_2$O$_2$) are added to a solution of 10 g of compound 101 (Example 1, Table 1) in 25 ml of acetone. The reaction mixture is stirred for 9 hours at 40° C. The reaction mixture is then treated with 100 ml of water and 50 ml of tolene. Most of the acetone is distilled off on a rotary evaporator under suction. The organic phase is separated off, washed with water, dried over sodium sulfate and concentrated by evaporation on a rotary evaporator under suction. Chromatography of the residue on silica gel with hexane/ethyl acetate/ethanol (12:7:1) gives 7.14 g (69%) of 4-{N-isopropyl-N-[3-(n-octylsulfinyl)-2-hydroxypropyl] amino}diphenylamine (compound 201, Table 2), brownish resin, molecular weight $C_{26}H_{40}N_2O_2S$ (444.68). Analysis calculated: C, 70.23; H, 9.07; N, 6.30; S, 7.21%. Analysis found: C, 70.04; H, 9.04; N, 6.42; S, 7.05%. EI-MS: 444 (M$^+$), 239 (M minus octyl-S(=O)CH$_2$CH(OH), base peak).

In a manner similar to that of Example 2 and using compound 102 (Example 1, Table 1), 62% of 4-{N-isopropyl-N-[3-(tert-nonylsulfinyl)-2-hydroxypropyl] amino}diphenylamine compound 202, Table 2) is obtained as a brownish resin. Molecular weight $C_{27}H_{42}N_2O_2S$ Analysis calculated: C, 70.70; H, 9.23; N, 6.11; S, 6.99%. Analysis found: C, 70.84; H, 9.19; N, 6.05; S, 7.35%. EI-MS: 458 ($M^+$), 332 (M minus $C_9H_{18}$), 239 (M minus tert-nonyl-S (=O)$CH_2CH$(OH), base peak).

In a manner similar to that of Example 2 and using compounds 103 to 111 (Example 1, Table 1), compounds 203 to 211 (Table 2) are obtained.

TABLE 2

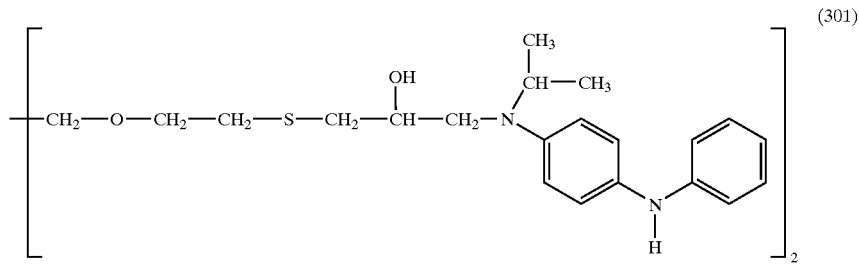

(201) to (211)

| Compound | R | $R^1$ | Constitution | $M^+$ |
|---|---|---|---|---|
| 201 | n-octyl | isopropyl | brownish resin | 444 |
| 202 | tert-nonyl | isopropyl | brownish resin | 458 |
| 203 | n-dodecyl | isopropyl | melting point 48° C. | 500 |
| 204 | tert-dodecyl | isopropyl | viscous oil | 500 |
| 205 | n-dodecyl | 1,3-dimethylbutyl | dark brown oil | 542 |
| 206 | tert-dodecyl | 1,3-dimethylbutyl | dark brown oil | 542 |
| 207 | n-octyl | 1,3-dimethylbutyl | dark brown oil | 486 |
| 208 | tert-nonyl | 1,3-dimethylbutyl | dark brown resin | 500 |
| 209 | n-dodecyl | 2-octyl | dark brown resin | 570 |
| 210 | n-dodecyl | cyclohexyl | dark brown resin | 540 |
| 211 | iso-$C_8H_{17}OOCCH_2$— | isopropyl | dark brown oil | 502 |

EXAMPLE 3

Preparation of 4,13-dithia-7,10-dioxa-1,16-bis[N-isopropyl-4-(phenylamino)-anilino]-2,15-dihydroxyhexadecane (Compound 301)

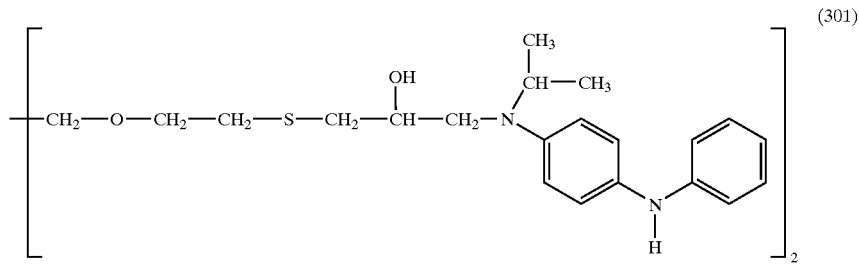

(301)

20.6 g (0.07 mol) of bisglycidyl thioether of 3,6-dioxa-1,8-octanedithiol are added dropwise over a period of 2 hours at 150° C. to 22.6 g (0.10 mol) of 4-isopropylaminodiphenylamine [Vulkanox 4010 (RTM), Bayer] and 0.28 g (2 mmol) of salicylic acid. The reaction mixture is then stirred for a further 6 hours at 150° C. The reaction mixture is cooled and chromatographed on silica gel using ethyl acetate/hexane (1:1). The pure fractions are combined, and the solvent is removed by evaporation on a rotary evaporator with suction. This gives 13.25 g (36%) of 4,13-dithia-7,10-dioxa-1,16-bis-[N-isopropyl-4-(phenylamino)anilino]-2,15-dihydroxyhexadecane (compound 301), viscous oil. Empirical formula $C_{42}HSBN_4O_4S_2$ (747.08). Analysis calculated: C, 67.52; H, 7.83; N, 7.50; S, 8.58%. Analysis found: C, 67.58; H, 7.78; N, 7.21; S, 7.93%. EI-MS: 746 ($M^+$), 239 ($C_6H_5NHC_6H_4N(C_3H_7)CH_2^+$, base peak).

EXAMPLE 4

Preparation of Compound 302

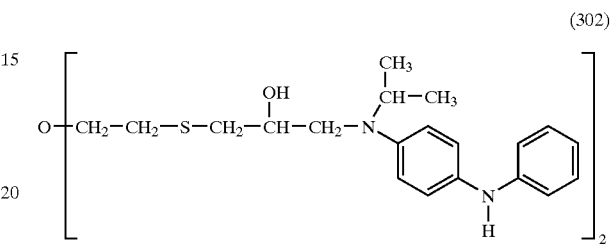

(302)

17.5 g (0.07 mol) of bisglycidyl thioether of 3-oxa-1,5-pentanedithiol are added dropwise over a period of 2 hours at 150° C. to 22.6 g (0.10 mol) of 4-isopropylaminodiphenylamine [Vulkanox 4010 (RTM), Bayer] and 0.28 g (2 mmol) of salicylic acid. The reaction mixture is then stirred for a further 6 hours at 150° C. The reaction mixture is cooled and chromatographed on silica gel using ethyl acetate/hexane (1:1). The pure fractions are combined, and the solvent is removed by evaporation on a rotary evaporator with suction. This gives 37.0 g (92%) of compound 302, viscous oil. EI-MS: 702 ($M^+$), 239 ($C_6H_5NHC_6H_4N(C_3H_7)CH_2^+$; base peak).

EXAMPLE 5

Preparation of Compound 303

28.1 g (0.13 mol) of glycidyl tert-nonyl thioether are added dropwise over a period of 2 hours at 150° C. to 9.2 g (0.05 mol) of 4-aminodiphenylamine and 0.14 g (1 mmol) of salicylic acid. The reaction mixture is then stirred for a further 2 days at 150° C. The reaction mixture is cooled and chromatographed on silica gel using ethyl acetate/hexane (1:3). The pure fractions are combined, and the solvent is removed by evaporation on a rotary evaporator with suction. This gives 6.1 g (16.5%) of compound 303, viscous oil. Empirical formula $C_4H8N_2O_3S_3$ (833.40). Analysis calculated: C, 69.23; H, 10.09; N, 3.36; S, 11.53%. Analysis found: C, 68.83; H, 10.09; N, 3.54; S, 11.68%. CI-MS: 833 ($M^+$), 127 ($C_9H_{19}^+$; base peak).

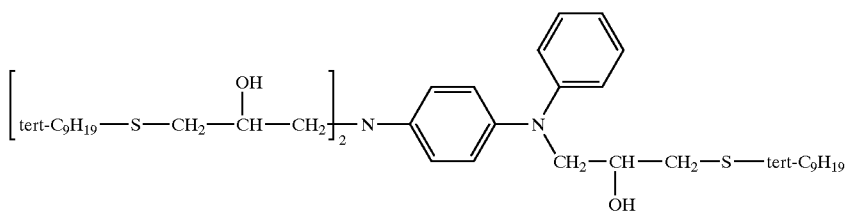

(303)

EXAMPLE 6

Stabilization of Black Vulcanizate 40.0 parts by weight of Cariflexs 1220 [polybutadiene, SHELL] are processed on mixing rolls at 60° C. with 60.0 parts by weight of natural rubber and 55.0 parts by weight of carbon black (N 330), 6.0 parts by weight of Ingralen 450 (RTM) [extender oil], 5.0 parts by weight of zinc oxide [vulcanization activator], 2.0 parts by weight of stearic acid [vulcanization activator], 0.2 parts by weight of IRGANOX 1520 (RTM) [processing stabilizer, Ciba Spezialit ätenchemiel, 2.0 parts by weight of sulfur (vulcanizer), 0.6 part by weight of Vulkacit MOZ (RTM) [vulcanization accelerator, BAYER] and 2.0 parts by weight of the stabilizer to be tested in accordance with Table 3, to give a homogeneous mixture, the vulcanization system (sulfur and Vulkacit MOZ (RTM)] not being added until the end of the mixing process. The mixture is vulcanized in electrical heating presses at 150° C. to T95 on the rheometer curves, to give elastomer sheets of 2 mm thickness, 21 cm length and 8.0 cm width. Sections of the 2 mm rubber sheets are placed on a white cardboard underlay and stored in a circulating-air cabinet at 50° C. for 5 days. The contact surface or its margin is then evaluated visually for contact discoloration (staining): 0=no discoloration (or the discoloration of the reference in which no AO is present) and 5=greatest degree of discoloration. The slighter the contact discoloration, the better the stabilization. The results are given in Table 3.

TABLE 3

| Example | Stabilizer (compound) | Contact discoloration - visual |
|---|---|---|
| 6a[a)] | — | 0 |
| 6b[a)] | Vulkanox 4020 (RTM)[c)] | 5 |
| 6c[b)] | 103 | 0–1 |
| 6d[b)] | 106 | 0–1 |
| 6e[b)] | 107 | 0–1 |
| 6f[b)] | 108 | 0–1 |
| 6g[b)] | 109 | 0–1 |
| 6h[b)] | 110 | 0–1 |
| 6i[b)] | 111 | 0–1 |
| 6k[b)] | 203 | 0–1 |
| 6l[b)] | 205 | 0–1 |
| 6m[b)] | 206 | 0–1 |
| 6n[b)] | 210 | 0–1 |

[a)]Comparative example
[b)]Inventive example
[c)]Vulkanox 4020 (RTM) [Bayer] is 4-[1,3-dimethylbutyl] aminodiphenylamine of the formula A
(A)

TABLE 3-continued

| Example | Stabilizer (compound) | Contact discoloration - visual |
|---|---|---|

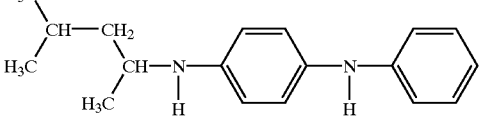

What is claimed is:

1. A composition comprising
    a) a naturally occurring or synthetic elastomer susceptible to oxidative, thermal, dynamic, light-induced and/or ozone-induced degradation, and
    b) as stabilizer, at least one compound of the formula I

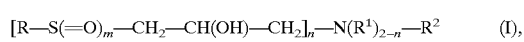

in which
R is $C_4$–$C_{20}$alkyl, hydroxyl-substituted $C_4$–$C_{20}$alkyl; phenyl, benzyl, α-methylbenzyl, α,α-dimethylbenzyl, cyclohexyl or —$(CH_2)_q COOR^3$, and, if m is 0, R may additionally

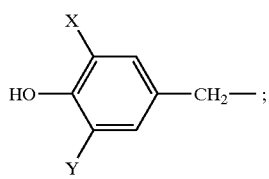

and, if n is 1 and $R^4$ is hydrogen, R may additionally be
$R^2$—$R^1$N—$CH_2$—$CH(OH)$—$CH_2$—$S(=O)_m$—$(CH_2)_x$— or
$R^2$—$R^1$N—$CH_2$—$CH(OH)$—$CH_2$—$S(=O)_m$—$CH_2$—$CH_2$—$(OCH_2$—$CH_2)_y$—,
$R^1$ is hydrogen, cyclohexyl or $C_3$–$C_{12}$alkyl, $R^2$ is 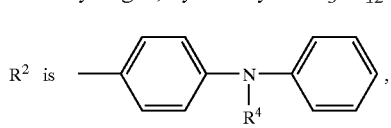, $R^3$ is $C_1$–$C_{18}$alkyl,
$R^4$ is hydrogen or —$CH_2$—$CH(OH)$—$CH_2$—$S(=O)_m$—R,
X is $C_1$–$C_8$alkyl,
Y is $C_1$–$C_8$alkyl,
m is 0 or 1,
n is 1 or 2,
q is 1 or 2, x is from 2 to 6, and
y is 1 or 2.

2. A composition according to claim 1, in which
R is $C_4$–$C_{12}$alkyl, hydroxyl-substituted $C_4$–$C_{12}$alkyl; benzyl, α-methylbenzyl, cyclohexyl or —$(CH_2)_q$COOR$^3$, and, if m is 0, R may additionally be

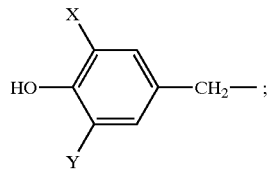

and, if n is 1 and R$^4$ is hydrogen, R may additionally be
$R^2$—$R^1$N—$CH_2$—CH(OH)—$CH_2$—S(=O)$_m$—$(CH_2)_x$— or
$R^2$—$R^1$N—$CH_2$—CH(OH)—$CH_2$—S(=O)$_m$—$CH_2$—$CH_2$—(O—$CH_2$—$CH_2$)$_y$—,
R$^1$ is hydrogen, cyclohexyl or $C_3$–$C_8$alkyl,
R$^3$ is $C_4$–$C_{12}$alkyl,
X is $C_1$–$C_4$alkyl,
Y is $C_1$–$C_4$alkyl,
m is 0 or 1,
q is 1 or 2,
x is from 2 to 4, and
y is 1 or 2.

3. A composition according to claim 1, in which
R is $C_6$–$C_{12}$alkyl, hydroxyl-substituted $C_6$–$C_{12}$alkyl; benzyl or —$(CH_2)_q$COOR$^3$, and, if n is 1 and R$^4$ is hydrogen, R may additionally be
$R^2$—$R^1$N—$CH_2$—CH(OH)—$CH_2$—S(=O)$_m$—$(CH_2)_x$— or
$R^2$—$R^1$N—$CH_2$—CH(OH)—$CH_2$—S(=O)$_m$—$CH_2$—$CH_2$(O—$CH_2$—$CH_2$)$_y$—,
R$^1$ is cyclohexyl or $C_3$–$C_6$alkyl,
R$^3$ is $C_6$–$C_{10}$alkyl,
m is 0 or 1,
q is 1 or 2,
x is 2, and
y is 1 or 2.

4. A composition according to claim 1, in which
R is $C_8$–$C_{12}$alkyl or —$(CH_2)_q$COOR$^3$, and, if n is 1 and R$^4$ is hydrogen,
R may additionally be $R^2$—$R^1$N—$CH_2$—CH(OH)—$CH_2$—S(=O)$_m$—$CH_2$—$CH_2$—(O—$CH_2$—$CH_2$)$_y$—,
R$^1$ is isopropyl or 1,3-dimethylbutyl,

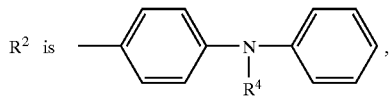

R$^3$ is $C_6$–$C_8$alkyl,
R$^4$ is hydrogen or —$CH_2$—CH(OH)—$CH_2$—S(=O)$_m$—R,
m is 0 or 1,
n is 1 or 2,
q is 1, and
y is 1 or 2.

5. A composition according to claim 1, in which component a) is a carbon black free elastomer.

6. A composition according to claim 1, in which component a) is a natural or synthetic rubber or vulcanizates prepared therefrom.

7. A composition according to claim 1, in which component a) is a polydiene vulcanizate, a halogen-containing polydiene vulcanizate, a polydiene copolymer vulcanizate or an ethylene-propylene terpolymer vulcanizate.

8. A composition according to claim 1, comprising other additives in addition to components a) and b).

9. A composition according to claim 8, comprising, as other additives, one or more components selected from the group consisting of pigments, dyes, fillers, levelling assistants, dispersants, plasticizers, vulcanization activators, vulcanization accelerators, vulcanizers, charge control agents, adhesion promoters, antioxidants and light stabilizers.

10. A composition according to claim 8, comprising, as other additives, phenolic antioxidants, aminic antioxidants, organic phosphites or phosphonites and/or thio-synergists.

11. A composition according to claim 1, in which the amount of component b) present is from 0.05 to 10%, based on the weight of component a).

12. A process for stabilizing elastomers to prevent oxidative, thermal, dynamic, light-induced and/or ozone-induced degradation, which comprises incorporating therein or applying thereto at least one component b) according to claim 1.

13. A process for preventing contact discoloration of substrates coming into contact with elastomers, which comprises incorporating into the elastomers, or applying thereto, at least one component b) according to claim 1.

* * * * *